(12) United States Patent
Sasian et al.

(10) Patent No.: US 8,098,369 B2
(45) Date of Patent: Jan. 17, 2012

(54) SYSTEMS AND METHODS FOR THE EVALUATION OF SCINTILLATION IN GEMSTONES

(75) Inventors: Jose Sasian, Tucson, AZ (US); Jason Quick, Las Vegas, NV (US); James Caudill, Las Vegas, NV (US); Peter Yantzer, Las Vegas, NV (US)

(73) Assignee: American Gem Society, Las Vegas, NV (US)

( * ) Notice: Subject to any disclaimer, the term of this patent is extended or adjusted under 35 U.S.C. 154(b) by 391 days.

(21) Appl. No.: 12/330,758

(22) Filed: Dec. 9, 2008

(65) Prior Publication Data
US 2009/0153835 A1    Jun. 18, 2009

Related U.S. Application Data

(63) Continuation-in-part of application No. 12/330,457, filed on Dec. 8, 2008, now abandoned.

(60) Provisional application No. 61/005,864, filed on Dec. 7, 2007, provisional application No. 61/012,323, filed on Dec. 7, 2007.

(51) Int. Cl.
    *G01N 21/00*    (2006.01)

(52) U.S. Cl. ........................................ 356/30
(58) Field of Classification Search .................. 356/30; 702/35; 705/1
    See application file for complete search history.

(56) References Cited

U.S. PATENT DOCUMENTS

| | | | | |
|---|---|---|---|---|
| 5,164,586 | A | * | 11/1992 | Hohberg et al. ............. 250/226 |
| 5,966,673 | A | * | 10/1999 | Shannon, Sr. ................... 702/35 |
| 7,251,619 | B2 | * | 7/2007 | Holloway ........................ 705/26 |
| 7,260,544 | B1 | * | 8/2007 | Reinitz et al. .................. 705/1.1 |

OTHER PUBLICATIONS

Sasian et al. Evaluation of Brilliance, Fire, and Scintillation in Round Brilliant Gemstones, Ootical Engineering 46(9), Sep. 2007.*

* cited by examiner

*Primary Examiner* — Layla Lauchman
(74) *Attorney, Agent, or Firm* — Lewis, Rice & Fingersh, L.C.

(57) ABSTRACT

Systems and methods, for the evaluation, grading, and presentation of evaluation results, of the scintillation of gemstones, such as diamonds. Specifically, there are discussed systems and methods for determining when a scintillation event in a gemstone is likely to occur and for mapping such events to a presentation.

21 Claims, 15 Drawing Sheets
(10 of 15 Drawing Sheet(s) Filed in Color)

SYSTEMS AND METHODS FOR THE EVALUATION OF SCINTILLATION IN GEMSTONES

CROSS REFERENCE TO RELATED APPLICATIONS

This application is a Continuation-in-Part of U.S. patent application Ser. No. 12/330,457 filed Dec. 8, 2008 now abandoned which in turn claims the benefit of U.S. Provisional Application Nos. 61/005,864 and 61/012,323 both of which were filed Dec. 7, 2007. The entire disclosure of all documents is herein incorporated by reference.

BACKGROUND

1. Field of the Invention

This disclosure relates to the field of gemstone evaluation, particularly to the evaluation of scintillation in gemstones such as diamonds.

2. Description of the Related Art

Diamonds have traditionally been graded based on what is known as the four C's: color, clarity, carat weight, and cut. Other than carat weight which is directed to the actual size of the stone, the other three factors attempt to quantify or rank diamonds which are objectively better than others. The parameters, therefore, are ways of indicating how light interacts with the diamond, whether the stone appears bright and lively, and whether the diamond appears to produce color or not.

While the four C's have a long standing tradition, they are, in many respects, a stand in for what is a subjective appearance to a user. Instead of talking about more objective grading standards, many users instead will focus on what they see in a diamond. This may relate to color or to "liveliness" of a diamond. A well cut diamond, when moved, will often appear to include many different colors of light in a number of different locations making the stone have what appears to be a large amount of internal movement, color, and prismatic effect.

Generally, a diamond's effect on light is characterized by referring to the stone having fire, brilliance, or scintillation. All of these terms relate to the stone's ability to reflect, refract, or otherwise act on incoming light in a particular fashion. Brilliance is generally the stone's ability to redirect white light toward a viewer, scintillation is generally the apparent movement or flashing of light in the stone, and fire is generally the ability of the stone to disperse light and produce colors which appear to be within the stone.

Interestingly, cutting a diamond for one effect will often lower the ability to see other effects. For instance, a very brilliant diamond, will often appear to not have much fire or scintillation. While color or movement may be being produced, the color and changes may be washed out by the high level of white light. Therefore, it often requires examination of a stone under many different lighting conditions to see its true attributes.

Because of the complexity of a diamond's geometry as well as the different kind of environments in which it may be viewed, purchasing diamonds is often very hard on a consumer. They may look at a diamond and think it is attractive, but are concerned that what they like is not objectively "better" or that they are being overcharged for an item which is as much an investment as a purchase For this reason, an ability to objectively evaluate and also to more systematically explain and display the properties of a particular diamond are desirable.

As the effect of scintillation is flashes of white or colored light that appear when the gemstone, the observer, or the illumination is in movement, it can often be difficult to demonstrate or quantify the scintillation of a diamond. The effect of scintillation is sometimes demonstrated by moving a gemstone under a given illumination scenario. This can provide the ability to compare the scintillation of multiple diamonds provided at a single time, but often does not allow for comparison of diamonds which are separated by physical or temporal space. Further, since the effect can be specific to lighting conditions, it often requires that the presentation be made in a live setting, which can be difficult in certain retail environments,

SUMMARY

The following is a summary of the invention in order to provide a basic understanding of some aspects of the invention. This summary is not intended to identify key or critical elements of the invention or to delineate the scope of the invention. The sole purpose of this section is to present some concepts of the invention in a simplified form as a prelude to the more detailed description that is presented later Because of these and other problems in the art, there are described herein, among other things, systems and methods for determining the size and location of facets and virtual facets within a gemstone and for mapping those facets in a graphical presentation which allows for the type and appearance of such facets to be quickly presented. As part of this, appearance of virtual facets can also be used, either in a single pictures or animation, to show approximately places where light flashes would be expected to occur and thus provide a general indication of the scintillation within a gemstone such as a diamond.

There is also described herein a methodology to evaluate scintillation in gemstones comprising: acquiring the angular spectrum of a gemstone by tracing single rays to the gem from a point in relation to the gem, propagating the rays in the stone till they exit the stone, and noting the exit angle of each ray; and coloring, or otherwise, coding an image of the gemstone according to angular ranges of the rays that exit the gemstone.

There is also described herein the method where a set of angular-range coded images of a gemstone is created where the gemstone is at different position with respect to the point, possibly where the images in the set are used to created an animation.

In another embodiment of the method the size, number, distribution, and mixing of the virtual facets in the coded gemstone image are used to evaluate scintillation. The size, number, distribution, and mixing of the virtual facets in the set of images may also be used to evaluate scintillation.

There is also described herein, a methodology to evaluate scintillation in gemstones comprising: acquiring the size of the virtual windows of a gemstone by tracing single rays to the gem from a point in relation to the gem, propagating the rays in the stone till they exit the stone, and noting the size of the virtual facets; and color coding, or otherwise coding, an image of the gemstone according to virtual facet size.

There is also described herein a method to evaluate scintillation in gemstones, the method comprising: acquiring the angular spectrum of a gemstone by tracing rays to the gemstone from a point of observation in relation to the gemstone; propagating the rays in the stone till they exit the stone; determining a region of a hemisphere arranged about the gemstone that the rays intersect; and coding an image of a virtual facet propagating the ray according to the region that the rays intersect.

In an embodiment of the method the gemstone is a diamond and the point of observation is located above the table of the gemstone.

In another embodiment of the method the region is located at a polar angle of between about 45 degrees and about 75 degrees and may be one of a plurality of regions within the polar angle range which plurality are arranged as concentric arcs or truncated pie sections. In an embodiment, there are six such regions within the polar angle range.

In another embodiment of the method the coding comprises color coding

In another embodiment, the method further comprises: tilting the gemstone relative the point of observation; and repeating the steps of propagating, determining and coding. The maps generated from this method may then be presented in a matrix of images where each of the images in the matrix corresponds to a different tilt of the gemstone or in a sequence to provide an animation.

There is also described herein, a method to evaluate scintillation in gemstones, the method comprising: obtaining a diagram of the virtual facets of the gemstone; and coding each of the facets based on its size.

There is also described herein a system for evaluating scintillation in gemstones, the system comprising: a computer, the computer being provided with a virtual image of a gemstone; means in the computer for acquiring the angular spectrum of a gemstone by tracing rays to the gemstone from a point of observation in relation to the gemstone; means in the computer for determining a region of a virtual hemisphere arranged about the gemstone that the rays intersect; and means in the computer for coding an image of a virtual facet propagating each of the rays according to the region that the rays intersect.

There is also described herein, a graphical display of a scintillation potential of a gemstone, the display comprising: a color-coded image, the color coded image being generated by: providing an image of a gemstone, the image showing virtual facets of the gemstone; acquiring the angular spectrum of a gemstone by tracing rays to the gemstone from a point of observation in relation to the gemstone; determining a region of a virtual hemisphere arranged about the gemstone that each of the rays intersect, and color coding the image of a virtual facet propagating the ray according to the region that the ray intersects.

In an embodiment the display further comprises: a plurality of color-coded images, each of the images being generated by providing, acquiring, determining, and color-coding the gemstone with a different point of observation. The plurality images may be presented in a matrix or sequentially in an animation.

There is also described herein a graphical display of a scintillation potential of a gemstone, the display comprising: a coded image, the coded image being generated by: acquiring the angular spectrum of a gemstone by tracing rays to the gemstone from a point of observation to said gemstone; determining a region of a virtual hemisphere arranged about said gemstone that each of said rays intersect; selecting a source on said virtual hemisphere; coding an image according to how many rays intersect that region; repeating said steps of selecting and coding for a plurality of sources.

There is also described herein a method for evaluating the scintillation of a gemstone, the method comprising: acquiring the angular spectrum of a gemstone by tracing rays to the gemstone from a point of observation to said gemstone; determining a region of a virtual hemisphere arranged about said gemstone that each of said rays intersect; selecting a source on said virtual hemisphere; determining how many rays intersect that source; repeating said steps of selecting and determining for a plurality of sources on said hemisphere; and evaluating the scintillation of said gemstone based on said repeating.

In an embodiment of the method, the evaluation comprises determining the average number of intersections across all said sources or an image of the hemisphere is coded based on the number of rays that intersect each said source.

BRIEF DESCRIPTION OF THE FIGURES

The patent or application file contains at least one drawing executed in color Copies of this patent or patent application publication with color drawing(s) will be provided by the office upon request and payment of the necessary fee.

FIG. 8A shows the map using concentric illumination ranges, FIG. 8B using sector illumination ranges.

FIG. 15 is looking directly down on the table. FIG. 16 is at 22.5 degrees of tilt and FIG. 17 is at 45 degrees of tilt.

DESCRIPTION OF PREFERRED EMBODIMENT(S)

The value of a gemstone generally depends first on its size, but next on its appearance. This is particularly true with diamonds since many diamonds lack intrinsic color and therefore are desired for their ability to handle light. The appearance of any diamond necessarily depends on factors intrinsic to the raw diamond, such as the clarity of the stone, and whether the stone includes any flaws in its crystalline structure. However, the appearance of a diamond which is intended to be used as an artistic optical structure will also depend greatly on its cut. A skilled diamond cutter can transform a raw diamond into a prismatic optical structure that interfaces with light to appear to have color and that focuses light to the observer. In this way a diamond becomes not only a stone, but a light sculpture.

While all these intrinsic factors of a diamond affect its appearance and, therefore, its quality and value, a diamond's appearance in any given situation also depends on extrinsic factors, such as how the diamond is being illuminated and how it is observed Many jewelers utilize high intensity light to show off their best stones. While this can be a good indicator of a stone's brilliance, it often results in a stone's other features being covered up. This can be particularly important in the purchase of diamond jewelry where the lighting of the diamond when it is worn may be quite different from the lighting when it is purchased.

Figure 1:
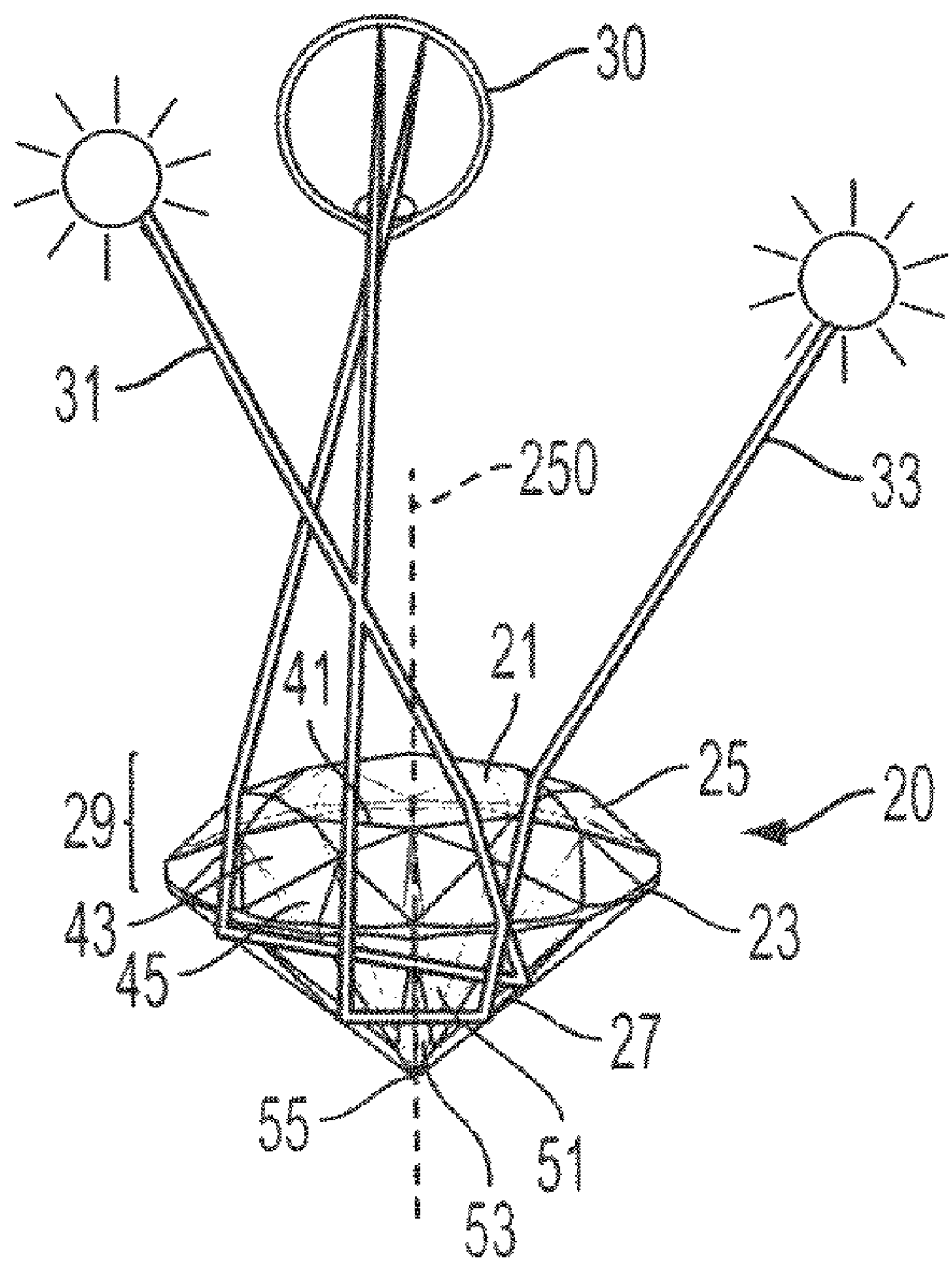
FIG. 1 shows a side view of a round brilliant diamond.

In a finished diamond, only the cut can be controlled by human intervention, and therefore the ability to know how to cut a diamond to provide the best look possible for any particular raw stone is of paramount importance to those who create diamond jewelry. In FIG. 1 there is shown a two dimensional wire frame representation of a diamond (20). The cut of a diamond (20) refers to not only the diamond's shape (e.g., diamond (20) is a brilliant round cut diamond as opposed to an oval or princess cut), but also to the relative proportion and orientation of the different portions of the diamond (20). A well cut diamond is cut to a particular shape, as well as having the various dimensions of that shape be to exacting relationships. These relationships are intended to allow the diamond to interact with light in what is generally seen as the most evocative manner possible. A well cut diamond is essentially a very complex optical structure constructed out of a very hard resilient material which is also generally transparent and provides for a large amount of light reflection, which is much of what gives it its appeal When referring to a diamond (20), there are a number of facets (41), (43), (45), (51) and (53), which are effectively planar faces, which create the diamond's (20) form and structure and, therefore, its optical effect. Obviously, it is generally not possible or desirable to cut inside the diamond's form. The shape, size, and spacing of the facets on its exterior surface, however, can dramatically improve, or hinder, the diamond's ability to act as an optical structure in a desirable fashion. Parts of a cut diamond generally include the table (21), bezel (23) (which combined form the crown (29)), girdle (25), and pavilion (27). All of the angles associated with these components, as well as the actual precision of the cuts themselves combine to make a diamond of a better cut.

Further, each portion of the diamond is also made up of a plurality of facets (41), (43), (45), (51) and (53) on each of these areas. These generally have a variety of different shapes and sizes and are what provides the optical effects of the stone. For a round brilliant cut, the bezel (23) generally comprises eight star facets (41), eight kite facets (43), and sixteen upper girdle facets (45). The pavilion (27) is divided into the lower girdle facets (51), the pavilion main facets (53), and the culet (55) which is the bottom point. The girdle (25) separates the crown (29) and the pavilion (27) and comprises a plurality of significantly smaller facets that are parallel to the main axis of the stone. The main axis (250) of the diamond passes through the center of the culet (55) and is perpendicular to the table (21). The diamond is generally symmetrically cut about this main axis (250) For the case of the standard round brilliant cut diamond there are, therefore, 58 facets, 33 in the crown and 25 in the pavilion.

The purpose of the various facets (41), (43), (45), (51) and (53) is to obtain a dynamic interaction with light when the diamond (20) is viewed. In a typical desired viewing situation the diamond (20) is facing an observer (30), and the observer (30) is "above" the diamond (20) and looks generally into the table (21) and into the diamond (20). Diamonds are generally cut to be observed in this fashion as observation from this direction allows the most interesting optical features to be observed.

Most jewelry designs place the diamond (20) in a mounting to allow for it to be observed in this way by placing the users body "below" the culet (55). When the diamond (20) is viewed, light, such as rays (31) and (33) enter the diamond (20). These may be through the crown (29) or through the pavilion (27). The rays (31) and (33) are then internally reflected and refracted by the facets until they are finally directed toward the observer (30) or elsewhere. If directed toward the observer (30), the rays will add brilliance or fire to the diamond (20). If directed elsewhere, they have little to no positive effect on the stone's appearance from that position.

The optical function of a diamond's (20) cut includes bringing white light to an observer's (30) eye (which makes the diamond (20) appear to glow or shine and is usually referred to as brilliance) and in providing for prismatic effects so that incoming white light is dispersed and different colors of light are observed in the diamond (20) (which is often referred to as fire). The dispersion effectively provides color in what is actually a colorless stone because the interaction of different facets (41), (43), (45), (51) and (53) of the diamond's (20) geometry results in light of some wavelengths from a particular source being reflected toward the observer (30), while light of other wavelengths is reflected in such a way that it is not incident on the observer. This dispersion of light allows for color to be observed which appears to originate inside the diamond (20).

While the brilliance and fire of a diamond (20) are desirable in and of themselves, part of what can make a diamond a beautiful optical structure is also the ability of the stone to shift the specific type of light being directed to a user's eye based on small changes in positioning. Since diamonds are generally worn on the body when are intended to be observed, slight movements of the wearer (which are often unintentional) can result in rather radical changes to the type of light which is directed to an observer (30), since the observer's (30) eye is generally a relatively small target. In this way the diamond (20) can appear alive to an observer (30) as the diamond's (20) structure serves to magnify small movements so the observer (30) not only sees light, but sees changes to that light on a near constant basis.

The effect of movement on the lighting properties of diamond (20) is generally called scintillation. As opposed to brilliance and fire, which relate to how much light (whether white or colored) a diamond directs towards a user's eye at any given instant, scintillation is the ability of specific facets of a diamond to start and stop reflecting light (whether white or colored) toward the observer (30) as the diamond (20), light source, or observer (30) changes position. A stone with a large amount of scintillation will appear to "twinkle" or move in a more pronounced fashion than a stone with less scintillation.

One insightful approach to analyzing illumination effects in diamonds (20) is to utilize the concept of geometrical angular spectrum. The angular spectrum can be considered as a gem signature and is dependent on the cut proportions. Generally, angular spectrum refers to the set of ray angle directions that can make the facets (41), (43), (45), (51) and (53) of the diamond (20) appear illuminated because light from that ray angle is reflected to the observer (30). For a given position of a diamond (20) in relation to an observer (30) there is a set of directions with which rays (e.g., (31) or (33)) can enter a diamond (20) and be directed to the observer (30). Generally, an entering ray upon being incident on the diamond (20) will be split into two due to Fresnel reflection.

The first part of the reflected ray will be considered as contributing to glare if it reaches the observer (30) and is thus generally undesirable to observe. The refracted ray component will be internally reflected until it is refracted out of the gem and will contribute to brilliance (if it comprises many wavelengths) or fire (if it comprises fewer wavelengths) if it reaches the observer (30). This ray, upon exiting the diamond (20), will also be split and the resulting reflected ray will continue to be refracted and split and so on. Thus, the angular spectrum of a diamond (20) contains ray directions corresponding to a first generation of rays split only once before exiting the diamond (20) (which are known as primary refractions), a second generation of rays split twice (which are known as secondary refractions), and other higher ray generations according to the number of ray splits which have occurred. The first ray generation will generally contain most of the energy of the original entering rays. Successive ray generations will contain significantly less energy since the amount of energy reflected will be reduced by each reflection. Diamond has an index of refraction of 2.4 so thus about 83% of the energy in any ray exits as the refracted ray and about 17% continues to travel within the diamond (20) in the reflected ray. Materials with a lower index of refraction will contain more energy in the refracted ray, but in diamond, the primary refraction accounts significantly for the appearance of a diamond (20).

In scintillation, the fire pattern changes dynamically and flashes of white light are perceived across the crown (29) of the diamond (20). These form the two major scintillation effects, fire and flash scintillation. To observe them it is required that the diamond (20), the observer (30), or the illumination conditions be in movement. Typically the observer (30) tilts the diamond (20) back and forth to observe scintillation and naturally optimizes for the direction that maximizes scintillation. Without brilliance, there cannot be fire since no light can be brought to the observer. Without fire there cannot be fire scintillation as fire scintillation is change in the fire pattern. Flash scintillation can occur without fire scintillation and it is due to light sources are not dispersed by a particular facet instead providing essentially scintillation with white light.

While scintillation is relatively easily seen when the diamond (20) is under direct illumination, the ability of a diamond (20) to produce scintillation is different. White diffused illumination will wash out scintillation effects. Further facets that subtend a small angle will contribute more to produce a flash effect, the rapid turn on and off of the light from a given facet, than sources that subtend larger angles. Thus, fire scintillation is generally more vivid than flash scintillation.

The amount of scintillation perceived is linked to the brilliance and fire of a diamond (20) because as these items increase, the amount of scintillation generally will also. However, scintillation strongly depends on the change of illumination conditions. This change is primarily produced on purpose by the movement of the diamond (20) as it is admired. The effects on scintillation due to the movement in turn can be enhanced according to the intrinsic light scrambling properties of the diamond (20). Light scrambling properties are a shorthand way of discussing the diamond's (20) ability to mix or scramble the angular spectrum as light is projected into the crown (29), The problem with evaluating a diamond's (20) scintillation is that scintillation depends on this large number of different factors. Since the diamond (20) is an optical structure comprising a large number of mirrored and prismatic surfaces, each of which will interact with light differently depending on the direction that light is incident on the diamond and the type of light incident, determination of a total scintillation appearance can require a large number of considerations. Further, scintillation is dependent on movement and is thus a non-static effect. Therefore, trying to grade diamonds and provide comparison between diamonds based on scintillation can be difficult since such grading and comparison requires consideration of a number of different variables simultaneously.

Figure 2A:
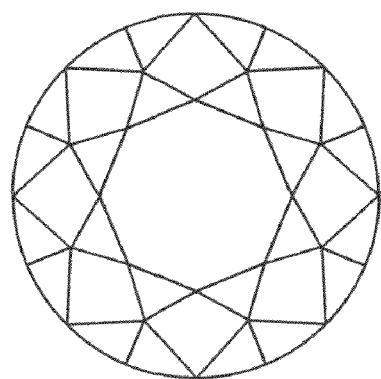
FIG. 2A shows the cut facets of a round brilliant diamond.
Figure 2B:
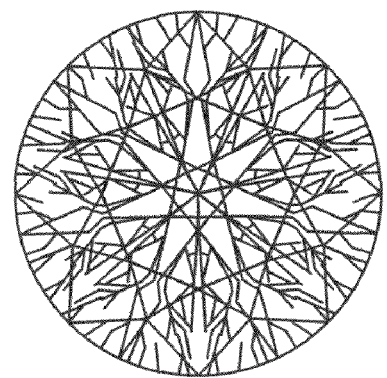
FIG. 2B shows the virtual facets of the same diamond upon primary refraction as projected on the crown.
Figure 2C:
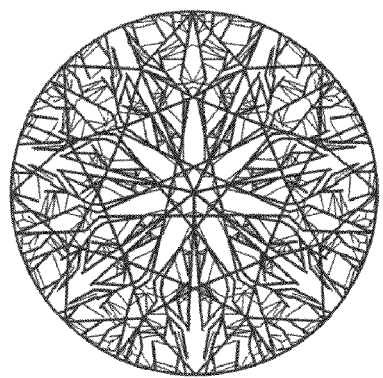
FIG. 2C shows the virtual facets of the same diamond upon primary and secondary refraction as projected on the crown.

In addition to considering the actual cut facets of a diamond (20), the observation of a diamond (20) reveals that its appearance appears to comprise many more facets than the actual number of cut facets. This occurs because as a beam of light enters the diamond (20) it is divided into a plurality of beams as discussed above. This separation of beams creates the appearance of virtual facets within the diamond (20). The number of virtual facets depends on the number of actual facets the diamond (20) has and on the number of times light is partitioned as it propagates in the diamond. FIG. 2 shows the appearance of a round brilliant cut when exposed to light with only certain facets being visible. In FIG. 2A only the cut facets are visible. In FIG. 2B, the primary refraction virtual facets are shown. In FIG. 2C the primary and secondary virtual facets are shown. There will also be higher level virtual facets present in the stone, however, as the light is continually subdivided it will become less bright and therefore the higher the order generally the more likely the virtual facet's effect will be washed out by other refracted light. Therefore, the primary and secondary virtual facets are by far the most important.

The size and distribution of the virtual facets have an impact on the visual appeal of the diamond (20). As the size of the virtual facets approaches the limit of the eye's resolution, fire and flash scintillation events tend to appear as pinpoint events. If the size of the facets is several times larger than the eye's resolution then the effect of facet interplay can be more readily observed. This later effect is desirable as the sudden change of appearance of groups of facets becoming dark, illuminated, or colored can provide for significant apparent movement in the diamond (20). This is reminiscent of the sudden changes in pattern produced by a kaleidoscope as it is turned, The small virtual facets upon secondary (such as those shown in FIG. 2C) and higher-order refractions contribute to pinpoint fire and scintillation which provides more flash or specific light points whole. The first refraction mostly contributes large virtual facets, which are key in producing facet interplay and apparent movement. Thus, the primary refraction is the most significant because of the amount of light it carries and the size of the virtual facets.

In this disclosure there are provided systems and method to evaluate the scintillation abilities of gemstones, particularly diamonds, for the purpose of grading by utilizing the appearance of virtual facets and the angular spectrum from which a particular virtual facet can direct light to an observer. The methodology is independent of illumination scenario and is based on the angular spectrum of a gemstone by indicating the ability of a particular virtual facet to produce a scintillation event. The angular spectrum provides the critical illumination directions that can make the virtual facets of a diamond appear illuminated when it is observed from a given point in relation to the gemstone.

Because scintillation is dependent on a gemstone's movement, it is often difficult for a purchaser to control illumination conditions in a purchasing situation. Even under essentially identical conditions, slight alterations in a position or relative movement of a diamond (20) can result in relatively major changes to appearance. It is therefore desirable for there to be a convenient way to display the scintillation, or more accurately scintillation potential, of the diamond and compare it to the scintillation potential of another. In this way two diamonds (20) can be compared effectively without having to actually replicate conditions of observation which may be potentially impossible.

In this application, the ability of a virtual facet of a diamond (20) or other gemstone to go from directing to not directing light (whether white or colored) to an observer (30) provides for an effectively two stage transition which creates scintillation, Basically the angle in which the facet goes from projecting light to the eye, to not projecting light or vice-versa is its transition point or scintillation event. The combination of all the virtual facets of a diamond (20) such that at any given angle there will be facets transitioning provides for the scintillation potential of a diamond (20). Thus, a diamond (20) whereby for a large number of angles there are a large number of facets at the transition point and those are transitioning at relatively high numbers will provide for a diamond with a relatively high scintillation. A diamond where transitions only occur at a relatively small number of angles, or whereby there are fewer transitions, will generally have a decreased scintillation potential. It should be realized that a diamond with a high scintillation potential may not actually appear to have more scintillation to an observer (30) because the scintillation may be buried in the diamond's brilliance or other characteristics, however the diamond (20) has the potential to produce more scintillation under the right conditions, and may actually produce more scintillation, even if it cannot all be seen.

Further, as scintillation is effectively the total of all such transitions for any given movement each transition is generically called a "scintillation event" where a transition of a facet provides a single scintillation event. Therefore, the more scintillation events which occur or the more likely a scintillation event is to occur, generally the more scintillation that is seen and therefore the diamond is considered to provide for increased scintillation.

The information on scintillation potential is provided with a display or map which allows for an objective view of scintillation potential. The display will generally be graphical in nature providing a visual indicator of scintillation potential of a diamond. This may provide for an indication for a single common angle for viewing the diamond (20), at a multiple of angles for viewing the diamond (20), may be provided as an animation showing such multiple angles in sequence, or may graphically represent the probability of events occurring at any location. This graphical presentation is generally referred to as a scintillation map.

While it is preferred that the scintillation map, which will show the scintillation potential, be provided as a colored graphical representation, in an alternative embodiment, however, the display may be alphanumerical or otherwise categorical to show a general indicator of the entire diamond's (20) scintillation potential at once.

Further, while this disclosure will generally contemplate scintillation grading and mapping on diamonds, since they are the gemstone where the appearance of scintillation is considered most important, it should be recognized that these systems may be used on any gemstone, or in fact any optical structure, to determine its scintillation potential.

Figure 3:
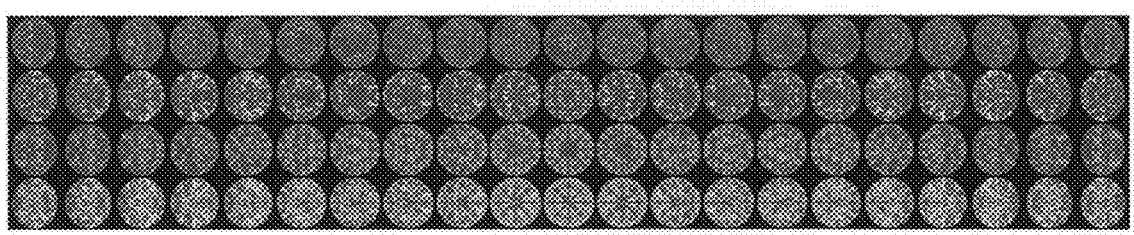
FIG. 3 shows a scintillation potential map where virtual facets are color-coded by size.

In a first instance of scintillation map, a diamond (20) is mapped for scintillation based on the number and size of its virtual facets. One such map which can be used for scintillation grading purposes is shown in FIG. 3. In this FIG., the diamond images have the virtual facets color coded by size at a variety of different tilts (as discussed later) of the diamond. Blue indicates small facets, yellow medium facets, and pink large facets. The last row is the superposition of the first three rows to show the general layout of the stone as a whole.

While this type of mapping can be useful, it does not provide for as much information as can be obtained using alternative methods. Specifically, while the map of FIG. 3 shows likely places where different types of scintillation will occur since it shows the various virtual facets, it does not actually show how much of a change in tilt is required to produce a scintillation event at any virtual facet. As scintillation is generally increased when produced by smaller movements, determining when a scintillation event is likely to occur is desirable.

U.S. Pat. Nos. 7,336,347; 7,382,445; 7,372,552; 7,420,657; and 7,355,683, the entire disclosures of which are herein incorporated by reference, provide for systems and methods for evaluating various properties of a diamond or other gemstone and provide for systems and methods for providing quantifiable relationships between different diamonds including various graphical representations of different aspects of a diamond or gemstone including graphically indicating fire or brilliance. Specifically, these patents discuss the light performance of a diamond (20) and how the diamond (20) acts to direct light which is incident upon it to the observer (30). As discussed therein, light performance takes into account the location of likely light sources when the diamond (20) is being viewed in a common viewing environment and then determines how much light from a particular source is directed to the observer (20) from these directions. As the amount of light in a normal viewing situation is generally different depending on where it is coming from, having the diamond (20) return light from angular ranges when there is likely a more powerful direct light source is generally preferred.

Figure 4:
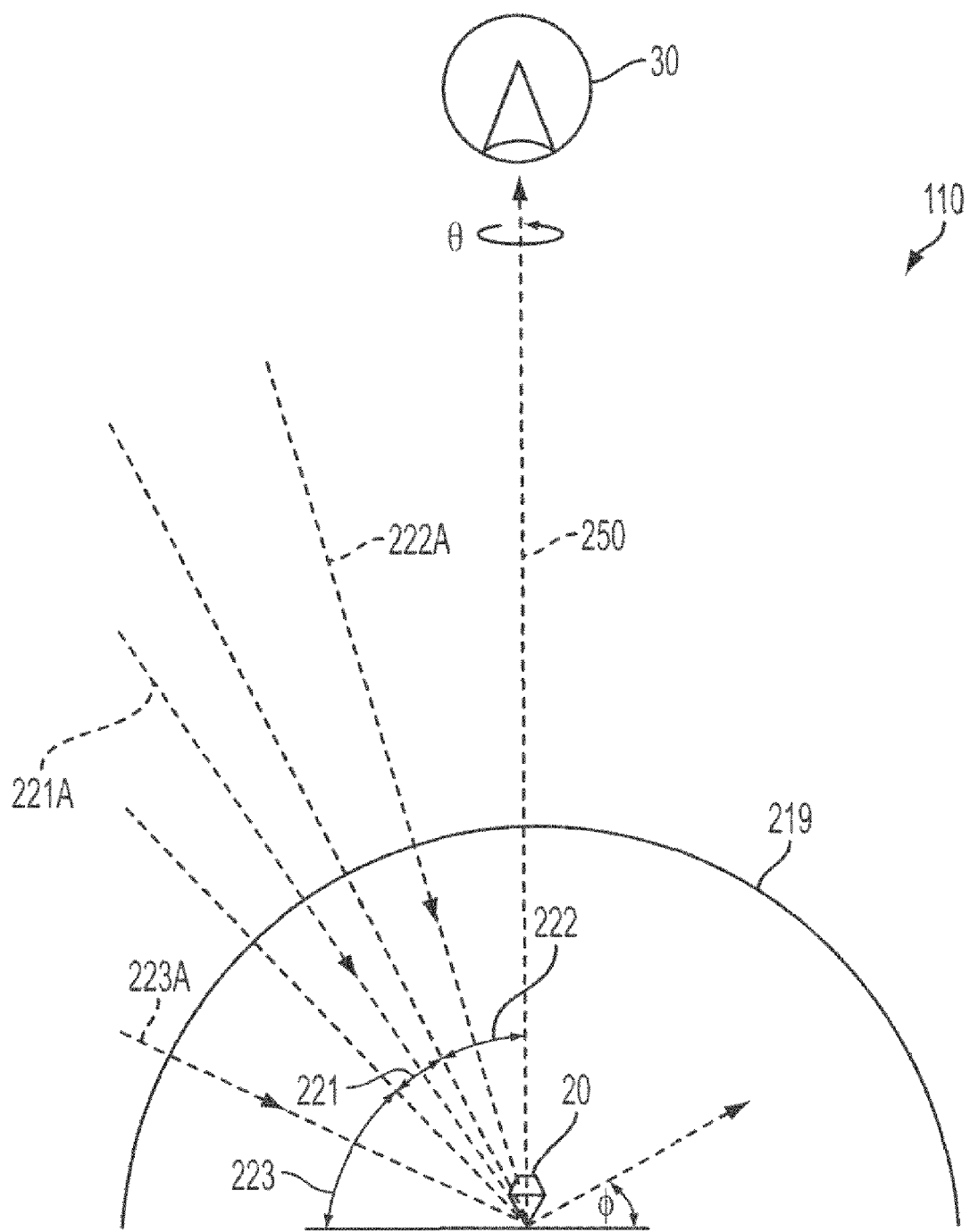
FIG. 4 shows a schematic diagram of an illumination hemisphere.

FIG. 4 provides for a general indication of the virtual hemisphere (219) of available light which is incident on a diamond (20). This works to determine which facets return light to an observer (30) under certain illumination conditions. In other words, the diamond (20) can be evaluated based on which incident light rays are directed towards an observer (30) by each facet. One can make such a determination by illuminating the diamond (20) with light from a number of different ray directions, and seeing which facets direct the incident light from that direction to an observer. Alternatively, as light paths are generally the same in both directions, the rays can be mapped from an observer (30) to the hemisphere (219) to determine where rays which would intersect the observer (30) originate from. In FIG. 4 diamond (20) is positioned beneath a hemisphere (219) of possible light which is incident upon it under most common viewing conditions.

As shown in FIG. 4, light rays from a first group of angles are incident on the diamond (20) within a first range of incident angles (221). Range (221) corresponds to a range of polar angles with respect to a hemispherical reference frame defined by the hemisphere (219) and centered on diamond (20). Polar angles, θ, are measured from a plane normal to axis 250, and azimuthal angles, θ, are measured within the plane. Light ray (221A) is incident on diamond (20) from the first range of polar angles (221) Light ray (222A) is incident on diamond (20) from a second range of polar angles (222), and light rays (223A) are incident on diamond (20) from a third range of polar angles (223).

As discussed in the patents referenced above, the light within the various angular ranges is generally of different quality. To generalize, polar angle ranges (221), (222), and (223) can correspond to any three ranges of polar angles in the hemispherical reference frame. In some embodiments, polar angle ranges (221), (222) and (223) can be selected to correspond to one or more characteristics of a typical viewing environment. For example, range (221) can be selected to correspond to the range of angles from where a diamond receives most of its illumination in a typical viewing environment (e.g., overhead indoor lighting or ambient outdoor lighting). In some embodiments, a lower limit of range (221)/upper limit of range (223) can correspond to polar angles of about 20° or more (e.g., about 25° or more, about 30° or more, about 35° or more, about 40° or more, about 45° or more, about 50° or more, about 55° or more, about 60° or more, about 65° or more).

Alternatively, or additionally, range (222) can be selected to correspond to overhead illumination that is occluded by a viewer's head. This range (222) can be selected based on the average size of a viewer's head and/or an average distance from which a viewer typically observes a diamond (20) (e.g., about 10 centimeters or more, about 15 centimeters or more, about 20 centimeters or more, about 25 centimeters or more, about 30 centimeters or more, about 35 centimeters or more, about 40 centimeters or more, about 45 centimeters or more, about 50 centimeters or more). In some embodiments, an upper limit of range (221)/lower limit of range (222) can correspond to polar angles of about 85° or less (e.g., about 80° or less, about 75° or less, about 70° or less, about 65° or less, about 60° or less, about 55° or less, about 50° or less, about 45° or less).

An example of polar ranges (221), (222), and (223) which correspond to illumination in a typical viewing environment that accounts for occlusion due to the viewer's head is as follows: range (221) from about 45° to about 75°; range (222) above about 75°; and range (223) below about 45°. In this example, range (222) corresponds to the occlusion due to a standard head size positioned 25 centimeters from the diamond. A standard head size refers to a head size that is the average of a man's head in the 5th percentile and a woman's head in the 95th percentile, according to the military standard MIL-STD-1472D.

Since incident light from range (221) generally will provide for the greatest return of light to observer (30), incident light from this area is generally going to be the source for most scintillation events. Therefore, which particular facets return light from within this range (221) are considered to provide the most important indicators of scintillation potential. However, in alternative embodiments, other ranges or combinations of ranges, may be used in determining scintillation potential.

In order to provide for rigor in analysis, while the scintillation analysis may utilize a real stone illuminated with zoned colored light (such as is contemplated in the above referenced patents), it is generally preferable to utilize a computer model of the diamond (20) which is then ray traced with hypothetical light rays to provide for scintillation analysis. This generally allows for finer analysis as well as for more controlled and exacting "lighting" conditions. However, in alternative embodiments, the scintillation analysis may utilize specific zone illumination on an actual stone with the resultant scintillation being observed directly or indirectly. Further, to provide for computational speed, instead of tracing all rays from all points in the hemisphere to determine which are incident on the observer (30) (or point of observation) rays may originate at this point of observation, be traced through the stone to the hemisphere (219) and then coded based on where in the hemisphere interaction occurs. In this way, only more relevant rays need be traced through the stone.

In the computerized process for evaluation, the evaluation begins by first taking a representation of the diamond's (20) geometry, and then determining how light will pass through the diamond (20). The geometry can be generated computationally using, for example, commercially available optical design programs such as ASAP™ (available from Breault Research Organization, Tucson, Ariz.), FRED (available from Photon Engineering, Tucson, Ariz.), LightTools® (available from Optical Research Associates, Pasadena, Calif.), TRACEPRO® (available from Lambda Research, Littleton, Mass.) or ZEMAX® (available from ZEMAX Development Corporation, San Diego, Calif.).

Figure 5:
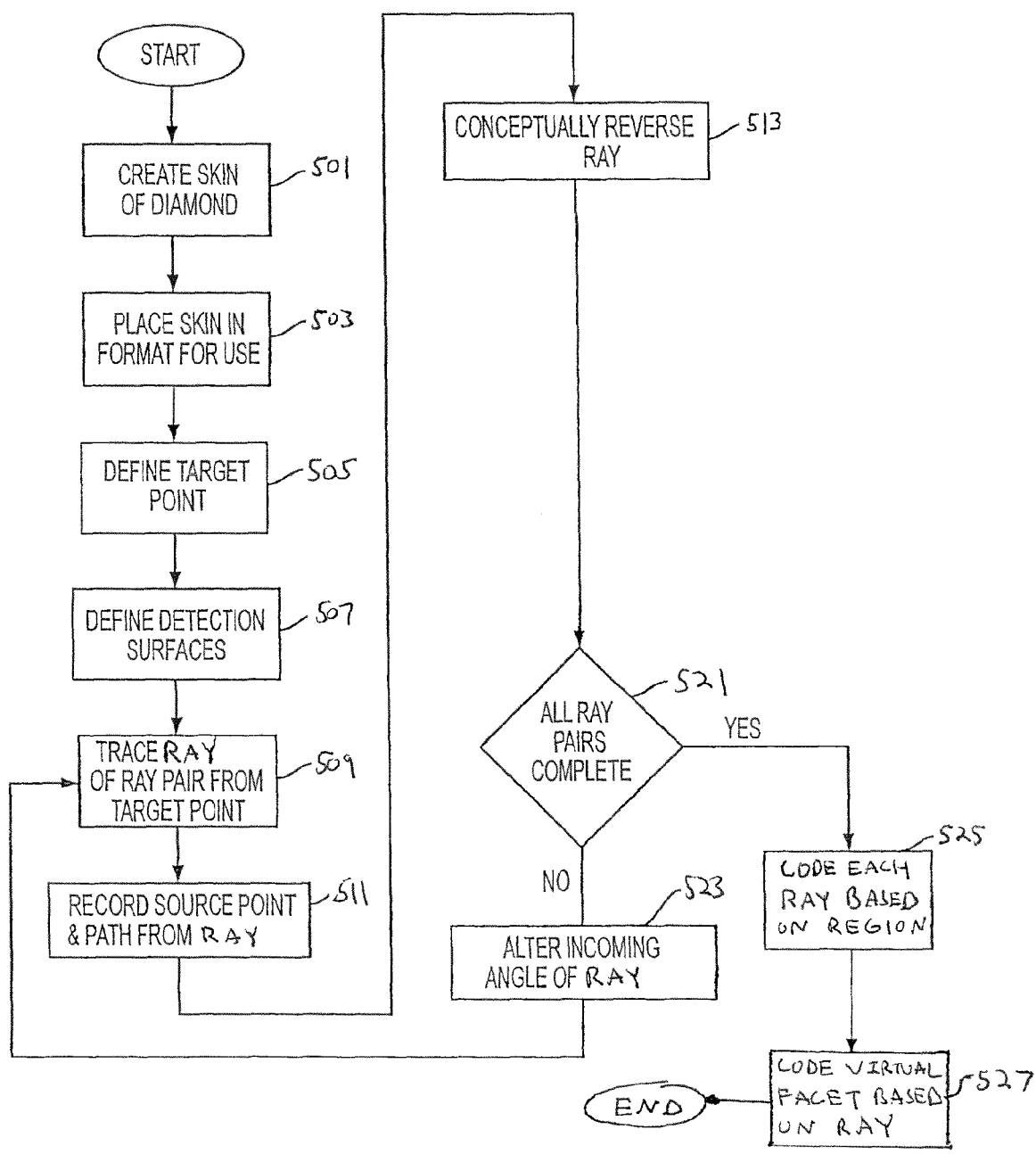
FIG. 5 provides for a flowchart for the steps of a computer ray trace analysis.

Referring to FIG. 5, a method for determining scintillation potential for light which leaves a particular portion of the diamond and is at least partially incident on the observer (30) is shown in flow chart form. In step (501) a "skin" of the diamond (20) is created. A "skin" refers to a data set including information about the diamond's geometry, such as the size and shape of each cut facet, and facet angles and locations. A skin may be acquired using a DiaMension™ tool running DiaVision™ software, both available from Sarin Technologies Ltd. (Sarin USA, New York, N.Y.). Methods for obtaining a skin are understood by those of ordinary skill in the art. The skin is effectively a representation of the diamond (20) which can be understood by a computer, processor, or other computational device which will now act upon it.

Once the skin is acquired, it is converted into a file format that can be used in an optical design program in step (503) so that ray paths representative of incoming light of different light waves and from different point sources can be determined and recorded. Again, this type of methodology is well understood to those of ordinary skill in the art, Prior to tracing ray paths through the diamond (20), the user defines a target point in step (505). The target point is a defined location which is effectively a stand in for the observer (30) and is the point of observation. The target point is preferably located over the center of the table (21) of the diamond (20) at a first predetermined distance. However, in alternative embodiments other locations can be used. The selection of target point is based on how a hypothetical observer (30) is viewing the diamond (20). In most cases the viewing is centered over the table to represent the "ideal" viewing location. However, other positions can be chosen to further show the properties of the diamond as will be discussed in conjunction with diamond tilt later in this discussion. The target point will, therefore, correspond generally to the observer (30) and will be used where a wavelength is incident on the observer (30). The distance between the target point and the diamond (20) can vary. Typically, the target point is located between about one centimeter and about 100 centimeters from the diamond (20), preferably between about 20 centimeters and 40 centimeters, and often at about 25 centimeters.

In an embodiment, more than one target point can be used which would result in target points at a plurality of distances and/or locations. In such an embodiment, an array of target points will generally be used. The outcome of one such embodiment is shown by the various maps shown in FIGS. 11-14 where the target point is moved off center (the diamond is tilted) providing the array of target points For simplification of discussion, however, a single target point is selected in FIG. 5. The process discussed herein would generally just be repeated for each target point if multiple points were used.

In some embodiments, rays can be traced for a diamond facing the observation point (e.g., where the source is located along a normal to table as measured from the center of the table). Alternatively, or additionally, rays can be traced with the diamond tilted with respect to the source. For example, the diamond can be tilted about 2° or more with respect to the source (e.g., about 3° or more, about 4° or more, about 5° or more, about 6° or more, about 7° or more, about 8° or more, about 9° or more, about 10° or more, about 11° or more, about 12° or more, about 13° or more, about 14° or more, about 15° or more, about 17° or more, about 20° or more).

Figure 6A:
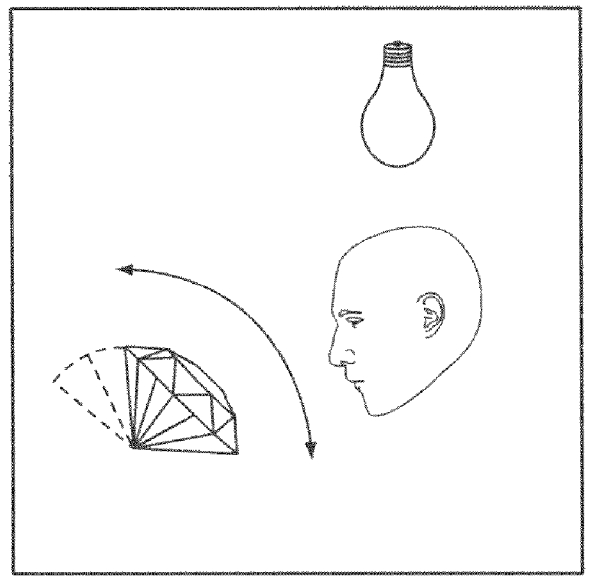
FIG. 6A shows front and back tilt of a diamond.
Figure 6B:
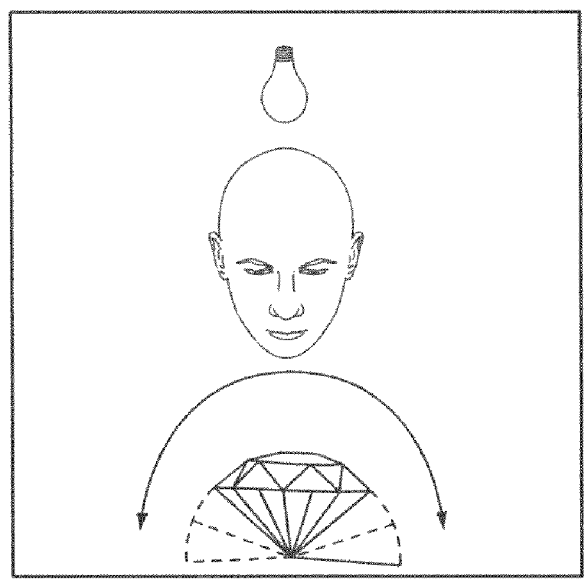
FIG. 6B shows left to right tilt of a diamond.

It should be recognized that as a 3-dimensional structure in space, there are three different axes around which a diamond (20) can be moved to potentially produce scintillation. The first of these is around the axis (250) which is effectively rotational movement. While this can produce scintillation, as a diamond (20) is generally intended to be cut to be relatively circularly symmetrical about this axis, this is generally a less important source of scintillation than the other two axes of rotation. As shown in FIG. 6A one of the axes is forward and back tilt. FIG. 6B provides for the other axis which provides for left and right tilt.

Prior to tracing ray paths through the diamond, the user defines a light source and detectors in the optical design program (507). The source can be a point source or a spatially extended source placed at the target point. The source can be monochromatic, colored (e.g., include multiple wavelengths in a wavelength band that is a subset of the visible spectrum), or a broadband source (e.g., including multiple wavelengths across the entire visible spectrum). In general, more wavelengths included in the source will increase the computational cost of the process. In some embodiments, a monochromatic source is selected for computational efficiency. In other embodiments, more than one wavelength is selected. For example, where dispersive effects are to be considered, two or more wavelengths can be used.

The distance between the source and the diamond (20) can also vary. Typically, the source is located between about one centimeter and about 100 centimeters from the diamond (e.g., between about 20 centimeters and 40 centimeters, such as about 25 centimeters).

Defining the detectors in the optical design program refers to defining a surface within a reference frame where rays traced through the diamond (20) are collected. In other words, the ray-tracing algorithm will record the location where a ray intersects a surface defined by the detector locations. In general, the geometry of the surface may vary as desired. As an example, in some embodiments, rays are collected on a surface of a hemisphere (219) centered on the diamond. An example of such a hemisphere (219) is depicted in FIG. 4.

In general, the radius of hemisphere (219) may vary as desired. For example, the radius of hemisphere (219) can be between about one centimeter and about 100 centimeters from the diamond (e.g., between about 20 centimeters and 40 centimeters, such as about 25 centimeters). In this example, the distance between the source and diamond is the same as the radius of hemisphere. However, in other embodiments, the distance between the source and diamond may be different from the radius of hemisphere. Optionally, an additional surface (e.g., a planar surface) can be defined to collect rays that exit the diamond along a path that does not intersect hemisphere (219).

In certain embodiments, detection locations can correspond to surfaces other than a hemisphere (219). For example, detection locations can correspond to one or more planar surfaces, such as surfaces that define a cubic or rectangular box. In some embodiments, detection locations can correspond to a spherical surface. The diamond (20) can be positioned at the center of the spherical surface, or at other location within the sphere.

Once the source and detectors have been defined, a computer algorithm traces rays through the diamond (509). The rays originate from the source, interact with the diamond (20), exit the diamond (20), and are collected when they reach a collection location (511). The algorithm can launch rays in different directions at random or systematically. Typically, rays are launched within a cone of directions corresponding to the area of the diamond (20) exposed to the source. This can ensure that all rays that are traced contact the diamond (20), increasing computational efficiency.

The algorithm traces rays based on physical laws that describe the interaction of electromagnetic radiation with matter. For example, the algorithm can trace each ray based on Snell's law of refraction and/or the law of reflection, which predict the path of a ray at an interface between two media.

The algorithm can account for ray splitting, for example, due to Fresnel reflections at an interface between two media. In some embodiments, the algorithm can account for multiple ray splittings, for example, due to higher order reflections. In other words, where a ray is partially reflected at an interface between two media, the algorithm can trace rays corresponding to both the transmitted portion and the reflected portion of the incident ray. Where the reflected portion is incident on another interface, it can again be split into a transmitted and reflected portion. The algorithm can continue to trace the second order reflection (i.e., the ray corresponding to the reflected portion of the initially reflected ray). A user can specify to what order reflections should be traced. In some embodiments, second order or higher reflections can be traced (e.g., third order or higher, fourth order or higher, fifth order or higher).

The algorithm can record the locations at which each ray intersects facets or virtual facets of the diamond. For example, the algorithm records where each ray intersects the diamond's crown (e.g., table and/or bezel).

In general, a sufficient number of rays to provide meaningful data should be traced. In some embodiments, the number of rays traced can be relatively large (e.g., about 100,000 or more, about 500,000 or more, about 1,000,000 or more). For example, in embodiments where one or more images of the diamond (20) are to be generated, a sufficiently large number of rays to fill the image should be used. However, in certain embodiments, fewer rays can be traced (e.g., about 50,000 or less, about 20,000 or less, such as about 5,000).

In order to generate a display of the diamond's scintillation potential, the rays detected at the hemisphere (219) can be reverse traced. In other words, the collection locations are treated as source points, and the source is treated as the collection location (513). The image of the diamond (20) is then generated by repeating the steps (521) of tracing and recording with a variety of rays of slightly different incoming angle (523) and identifying rays originating from the source but contacting the diamond (20) at slightly different points. For each ray, the angular range where it contacted the hemisphere (219) is determined and which virtual facet they interacted with en route to the original source point is selected, coding the ray based on the appropriate angular range (525) and then coding the drawing of the diamond (20) so the virtual facet interacting with that ray is coded similarly (527).

Figure 7A:
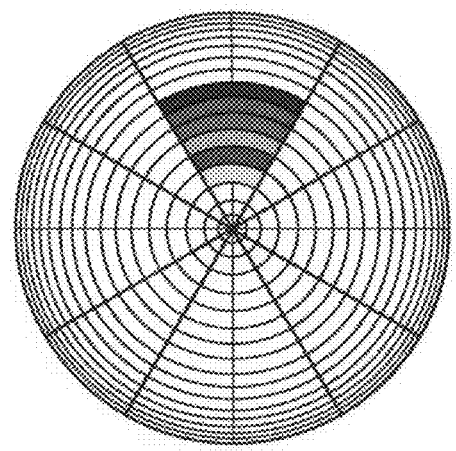
FIGS. 7A and 7B show the color illumination key for the scintillation maps of FIGS. 8A and 8B.
Figure 7B:
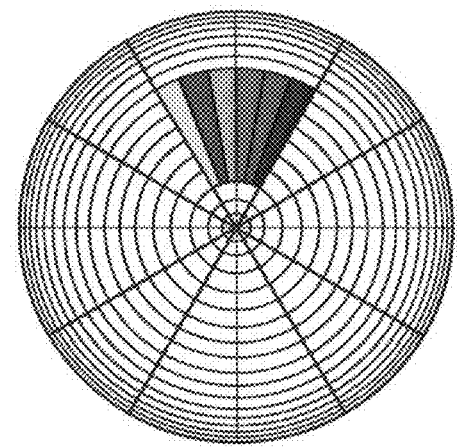

As shown in FIG. 7 the most basic scintillation maps are generated by determining from which facets light reaches the observer's eye when the diamond is in the face up position and the light is incident from the preferred angles (221), (45 to 75 degrees is used in the this figure for this range), in the hemisphere (219) and in a 60-degree arc sector as shown in the FIG. The light in this range (221) is presented in six colors (red, green, blue, cyan, magenta, and yellow) to further subdivide the range (221) into six sub regions (721A, 721B, 721C, 721D, 721E, and 721F) that are concentric arc circles in FIG. 7A. A virtual facet which returns light from fewer of the these sub regions will generally provide for a scintillation event with front and back tilt more readily than a virtual facet which returns light from all or none of sub regions. Further, the six sub regions (721G, 721H, 721I, 721J, 721K, and 721L) of FIG. 7B are truncated pie sections. A virtual facet which returns light from fewer of these sub regions will generally be more likely to provide for a scintillation event when left or right tilt occurs.

Figure 8A:
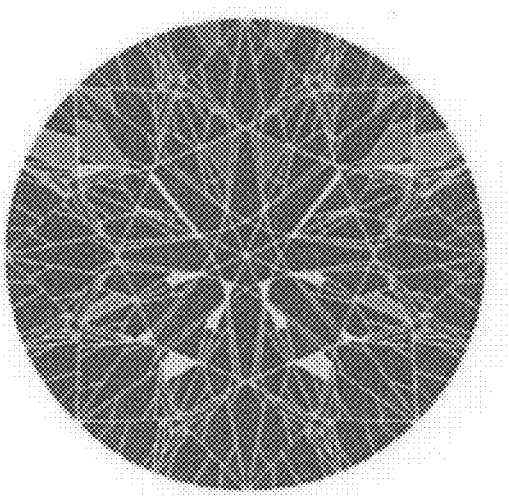
FIGS. 8A and 8B show scintillation maps in the face-up position, in color
Figure 8B:
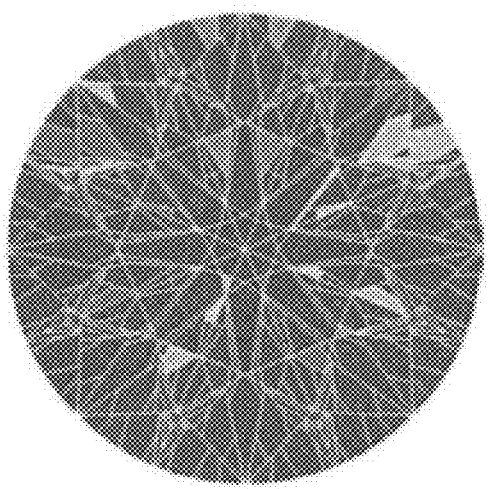

FIGS. 8A & 8B provide for the two returned scintillation maps for a hypothetical round brilliant diamond utilizing rays returned from (that is which exited into when sourced at the observation point) the sections of FIGS. 7A & 7B. The interpretation of the scintillation maps requires some explanation. The scintillation maps represent the change in illumination of the crown as a light source scans, in azimuth or radially, the medium angles in the hemisphere. A stone deemed to substantially scramble light would appear with a large number of colors well distributed over its crown in the scintillation map view as this would indicate that each virtual facet is reflecting a relatively small incident light angle corresponding to the appropriate subrange (721A-L) and thus has a relatively small angular spectrum. In FIG. 8, a round brilliant diamond is shown with both types of illumination shown the relative A and B figures showing the results from the relative sub region analysis. The size and form of the virtual facets is clearly shown as well as the illumination distribution over the crown of the diamond (20). Thus, a scintillation map (801) conveys information about the size and form of the virtual facets and about the intrinsic light scrambling properties of the diamond (20) as well as indicating how diamond (20) would exhibit scintillation.

In this method an image of a gemstone under evaluation is color coded according to angular ranges in its angular spectrum. Alternatively, the map may be generated using other representations such as figures, shades, symbols, or other coding from the angle sub regions. Virtual facets that are not colored represent areas in the gemstone that do not have a selected angular spectrum range based on the specific incoming light direction and the current positioning of the diamond (20) relative thereto. Colored virtual facets represent areas in the diamond (20) that have the associated angular spectrum range of return. A colored facet is therefore considered to have a scintillation event.

Figure 9:
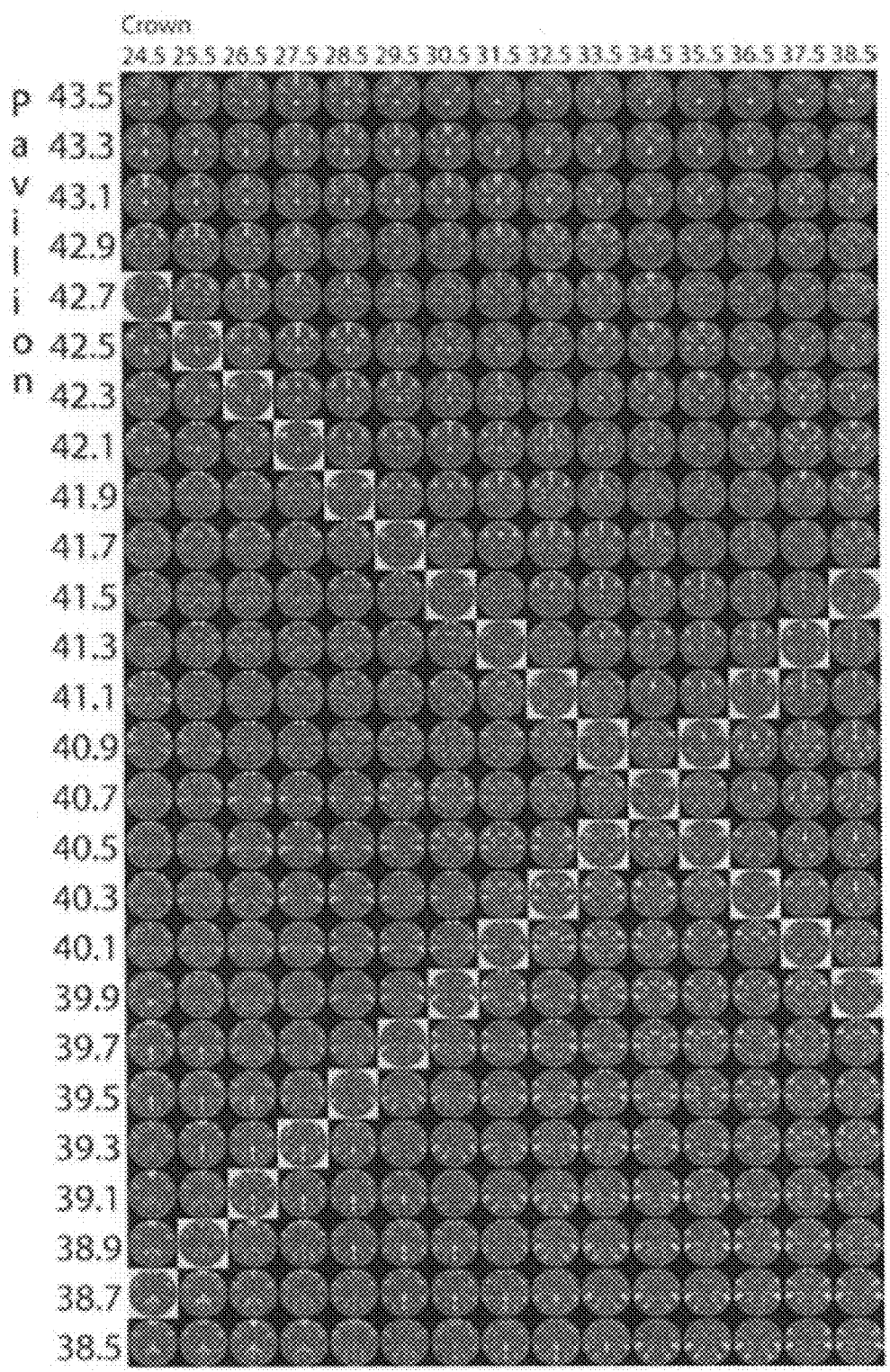
FIG. 9 shows a matrix of color face up primary reflection scintillation maps for diamonds of different dimensions.

To determine how best to cut diamonds (20) to maximize scintillation, maps (501) with a variety of different dimensions may be provided. These may then be arranged in a matrix to show how different proportions of cut effect the resulting scintillation. FIG. 9 shows a scintillation matrix produced upon the face-up position. Each of the primary refraction virtual facets that captures light from the selected hemisphere in the selected position appears colored and thus comprises a scintillation event. Diamonds that have more well-distributed scintillation events and color over the stone's crown have the potential to produce more scintillation than stones with lesser events and would generally be considered to have better scintillation potential. For example, FIG. 9 shows that stones at or near the main cutter's line have spatially well-distributed events as compared to other diamonds.

Figure 10:
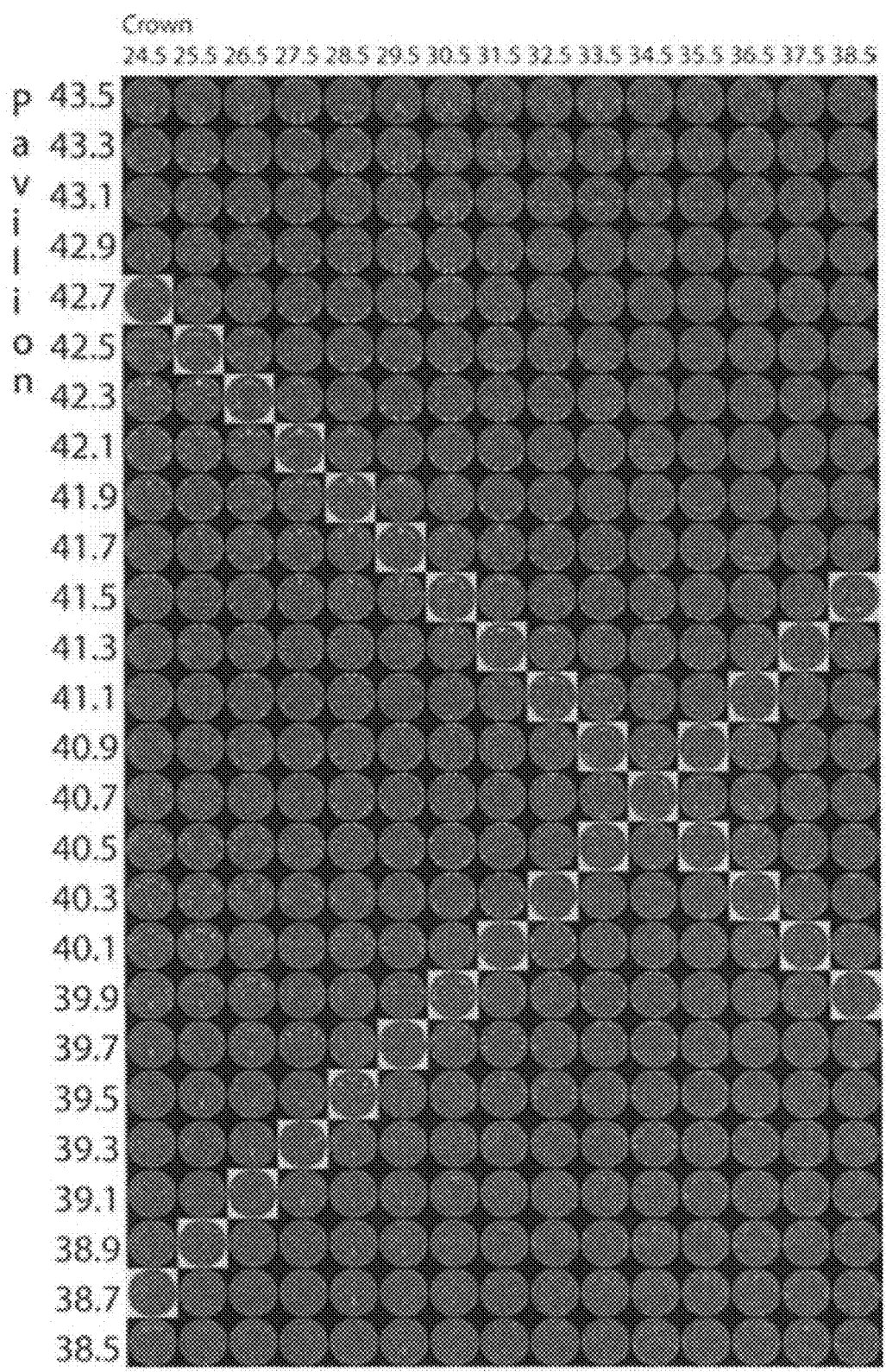
FIG. 10 shows a matrix of color face up secondary refraction scintillation maps for stones of different dimensions.

FIG. 10 takes the matrix one step further and shows a scintillation matrix upon secondary refraction. While these events will generally be less prominent than those on primary reflection, this can provide for additional scintillation in the diamond (20). The matrix of FIG. 10 shows that the virtual facets become smaller and scintillation may appear as a pinpoint effect upon localized bright sources. Given that light upon secondary refraction is reflected more times inside the stone, the scintillation will generally appear as more rapidly changing compared to scintillation from the primary refraction.

Although the maps in the face-up position such as FIGS. 9 and 10 are a primary tool for evaluating which are preferred cuts, they do not provide all information about the performance of a diamond (20) as it moves. Effectively, these matrices show only that the facet is reflecting a relatively narrow band of light and therefore is capable of creating a scintillation event. In order to show that there actually are scintillation events, it is desirable to show that with a slight change of rotation, a facet not only returns light to a user, but that the return changes when the position is altered. This is performed by using a tilt view.

As discussed above, there are two possible dimensions of tilt. Therefore, these are provided with two possible different tilts and thus two possible tilt views. However, due to a diamond's generally symmetrical curve, the two tilts generally will have similar interactions with light.

Figure 11:
FIGS. 11 & 12 show tilt views of a diamond with different angular subrange illumination indicators being used.
Figure 12:

The tilt-views that are presented provide a view of the gem properties as a function of the tilt with respect to the hemisphere and the observer. The tilt views are generated by tilting the stone from −30 deg to 30 deg in 3-deg increments. FIG. 11 provides for the same stone across a single tilt axis, with the other axis being held constant and with only one subrange of angles being used, in this way, the specific scintillation from rotation about that particular axis can be determined. FIG. 12 shows the same tilt views with different subranges being used.

The scintillation tilt maps of FIGS. 11 & 12 are generated by tilting the stone along the symmetry line of the illuminating, truncated pie sector in the hemisphere (219) as shown in FIG. 8B. This is equivalent to tilting a stone forward and backward as it is observed. The left maps (−15 to −30 deg of tilt) in the tilt view correspond to the backward tilts, the middle map to the face-up position, and the right maps (+15 to +30 deg of tilt) to the forward tilts. It can be appreciated that the larger number of scintillation events occur upon the face-up position (no tilt) and forward tilts to about 15 deg. The scintillation events observed in the tilt maps correspond to the events that one would observe when the stone is tilted quickly left to right while holding it at a given forward-backward tilt position.

Figure 13:
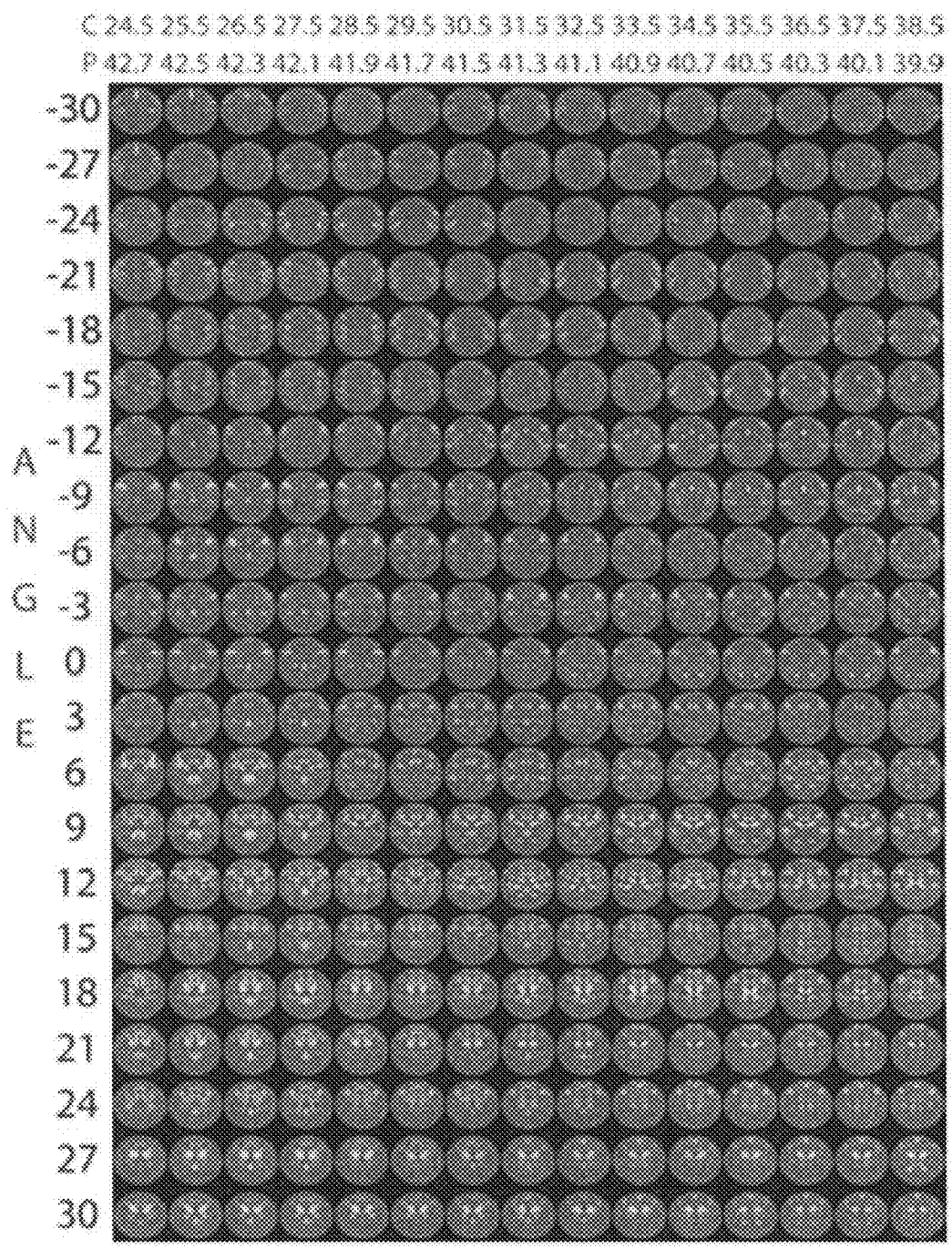
FIGS. 13 & 14 show maps for a number of different diamond cut dimensions at multiple tilts under both concentric and sector illumination.
Figure 14:
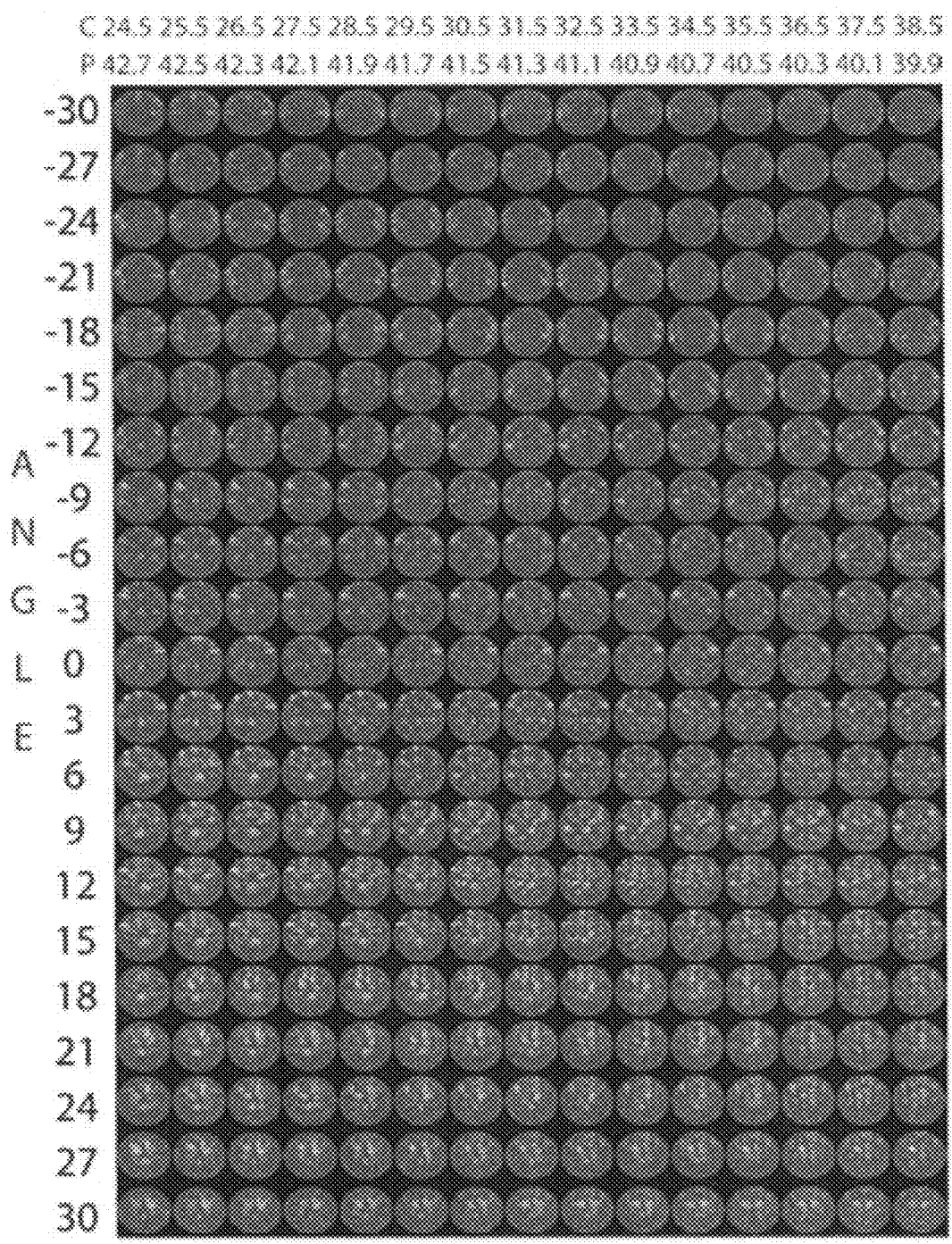

The views of FIGS. 11 & 12 can also be placed into a number of different diamonds can be compared using the same returns tilts. This is shown in FIGS. 13 & 14. Further, matrices may be created with the same diamond along different tilts. This provides for a large number of ways to provide comparison information both with an individual diamond and across diamonds.

In FIGS. 13 & 14, a selection of stones (along the cutter's line which is generally preferred dimensions) show the scintillation for concentric and sector illumination respectively. These maps, therefore, can show which specific cut proportions provide for more scintillation overall. The scintillation tilt-view maps show that diamonds that exhibit the best scintillation are the last seven in the main cutter's line given the better distribution of scintillation events at tilts around the face-up position.

While in the scintillation tilt maps the light source is assumed to be located in the range (221), the exact location and size of the light source does not actually change qualitatively the series of scintillation events seen in the tilt view maps. These scintillation events are concentrated in the table when the stone is tilted forward, spread over the crown as the stone has less tilt, and then appear in the bezel (left and right bezel areas) as the stone is tilted backward. Thus the tilt-view scintillation maps represent in a color-coded manner what an observer (30) would actually see in examining a stone. The number of events and their distribution in the scintillation tilt views indicate the scintillation properties of a stone.

Additional information can be provided from the tilt view matrices by placing the figures of the views into animation. These animations are not the same as computer simulations or films of gemstones in movement under particular illumination scenarios. Scintillation animations provide a general view of the scintillations abilities of a diamond by allowing one to generally see changes in facet refraction as the diamond (20) moves. They are color coded maps that show critical directions in the angular spectrum of a gem for different gem positions while moving between the positions. Therefore, the animation is not showing scintillation as it would appear in the diamond, but are showing the occurrence of events as well as the specific source of the light which is causing the scintillation event. Therefore, the diamond is not simply showing scintillation under a specific illumination condition, but is showing the scintillation potential of the diamond (20). That is, its comparable ability to produce scintillation compared to other diamonds (20).

The matrix and animation are particularly useful tools in that they provide for a large amount of information and allow for side by side comparisons of different stones. Further, animation of the matrices allows for presentation of the information in a more familiar fashion and also can simplify the display. However, while these methods provide for a large amount of information in a relatively small amount of space, they can be difficult for one not used to looking at them to understand Further, the specific changes of color of a facet do not necessarily represent an actual color change, but simply show that the likelihood of various events in increased in that region and require generally more complicated presentation technologies to display.

In another embodiment for scintillation quantification, various probability distributions are computed based on a source's potential to generate scintillation events. These probability distributions give several pieces of information related to scintillation at once. Effectively, these maps work as follows. If one assumes a randomly placed source of a specified size is placed in the preferred region of illumination, the following quantities are then provided for the diamond: the expected number of scintillation events generated by the source; the probability that 0,1,2,3,4, or more scintillation events will be generated by the source; the expected average distance between the scintillation events, and the expected area of the minimum polygon bounding the scintillation events. The first two of these quantities can be useful for evaluating the potential of a stone to scintillate. The last two can be useful for evaluating the distribution of scintillation events.

As discussed above, distribution of scintillation events can provide for additional information about the resultant scintillation of the diamond. As contemplated previously, when scintillation events are more widely distributed, there is often an apparent increase in the viewed scintillation. This is simply because the various events appear separate as opposed to being merged together by the eye of the observer.

In many respects, this embodiment can be thought of as a generalization of some of the other approaches that have been discussed. Rather than defining specific sub regions of the hemisphere (as is shown in FIG. 7) to use to generate color code gem maps such as those of FIG. 8, this method instead simultaneously considers all possible locations of a light source and summarizes the results into two key pieces of information. Therefore, it can help reduce bias from preferred lighting requirements. Firstly, it can provide the average number of events occurring from any source and secondly it can provide the probability distribution of seeing 0, 1, 2, etc events from across light sources One potential weakness of choosing a single sub region of the hemisphere is that for certain stone geometries, the particular location of the sub region may lead to a favorable assessment of the diamond's potential to scintillate, whereas a different sub region may lead to a different conclusion. For example, the location of the sub region may happen to intersect several ray directions from the stone, but if it were shifted a few degrees in one direction or the other fewer rays would intersect, thereby resulting in fewer illuminated virtual facets. Because of these observations along with the general observation that sources in ordinary lighting environments can occur almost anywhere in relation to the diamond, it is apparent that a more generalized approach may be more useful in certain situations for determining the expected number of scintillation events one may observe in the stone for a randomly placed source. This can also allow comparisons between stones to occur easier.

A natural way to generalize then, is to consider a stone's ability to exhibit scintillation events when it is illuminated by a randomly placed source. This removes the bias of choosing just one source or sub region of the hemisphere. Generally in this approach, it is much harder to produce a meaningful image of the gem itself and the corresponding virtual facets which can make the image appear more abstract and less connected to a particular diamond. However, there is generally gained an image of the illumination environment (hemisphere) which gives insights into how events may observed in the diamond for a given location of a source which can provide for more accurate direct comparison of diamonds, even if they have different cuts. What is also gained are meaningful values which give valuable information of what one might expect to observe in the gem, if it were observed in a random lighting environment, such as those generally encountered in the ordinary world when the diamond is being worn and observed.

For example, if one were comparing two gems and one exhibited an average of scintillation events across sources and another gem only exhibited an average of 2 scintillation events, then in most ordinarily encountered lighting environment, one would expect to see more scintillation events in the first gem compared to the second even though under certain specific lighting conditions the second could produce more. Furthermore, if the average area of the minimum bounding polygon were greater for the first gem than the second, then one would expect that the scintillation events would be better spread out and better distributed across the crown.

The probability distribution that is part of the generalized method also gives important information for the assessment of scintillation in a gemstone. Some facet arrangements and geometries naturally tend to exhibit a large number of simultaneous scintillation events, while others tend to yield fewer events at any given time. In other words, for one gem, a randomly placed source of a given size may exhibit 7 or more events 8.0% of the time, while a randomly placed source for another gem may never exhibit more than 4 events. Clearly then, it's much more likely to several simultaneous scintillation events in the first gem than the second, which is very useful information for assessing the scintillation potential of a gemstone. Effectively, not only is the average number of scintillation events valuable, but the distribution (such as may be evidenced by the standard deviation) can also be useful.

Figure 15:
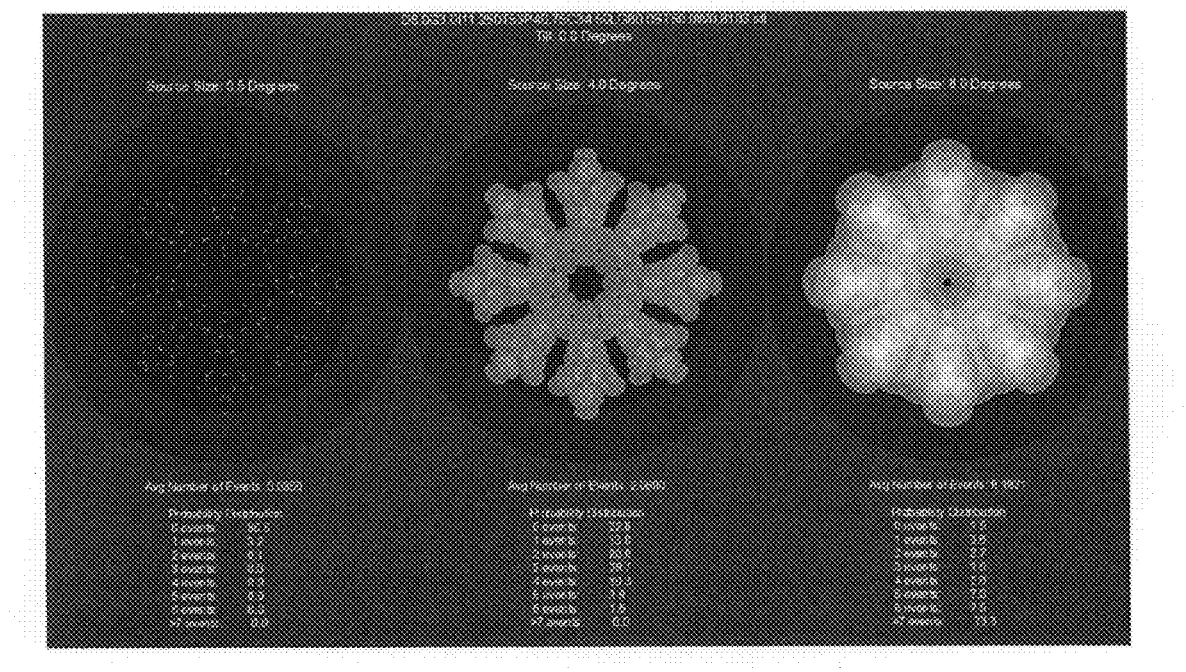
FIGS. 15-17 shows hemisphere maps color coded according to scintillation event counts.
Figure 16:
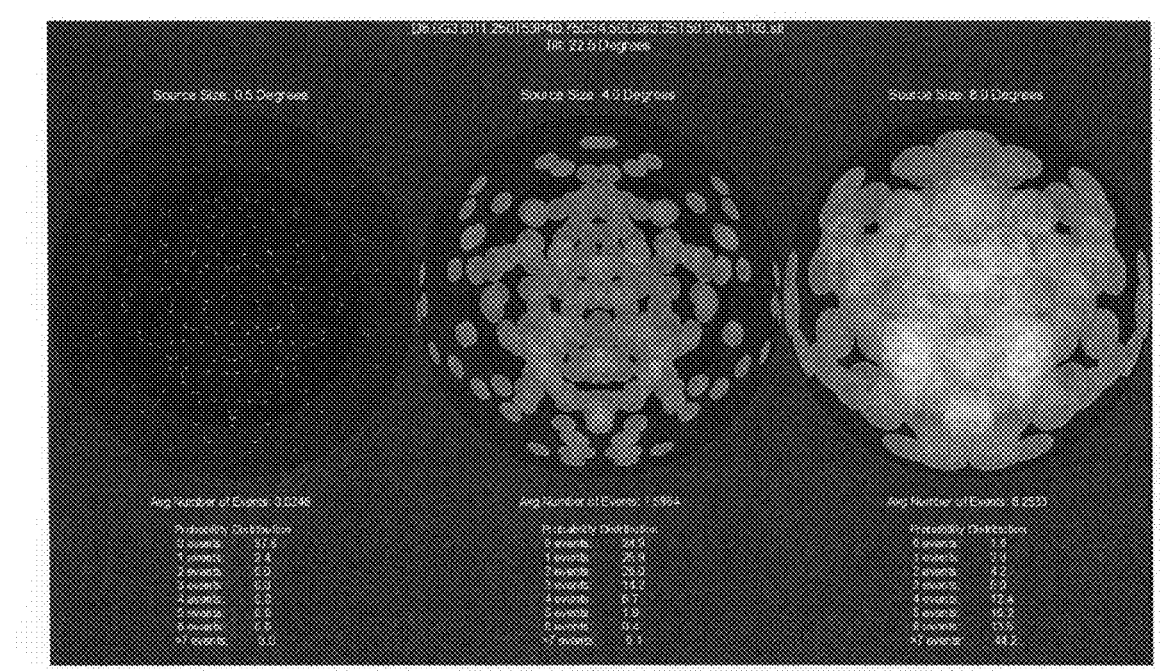
Figure 17:
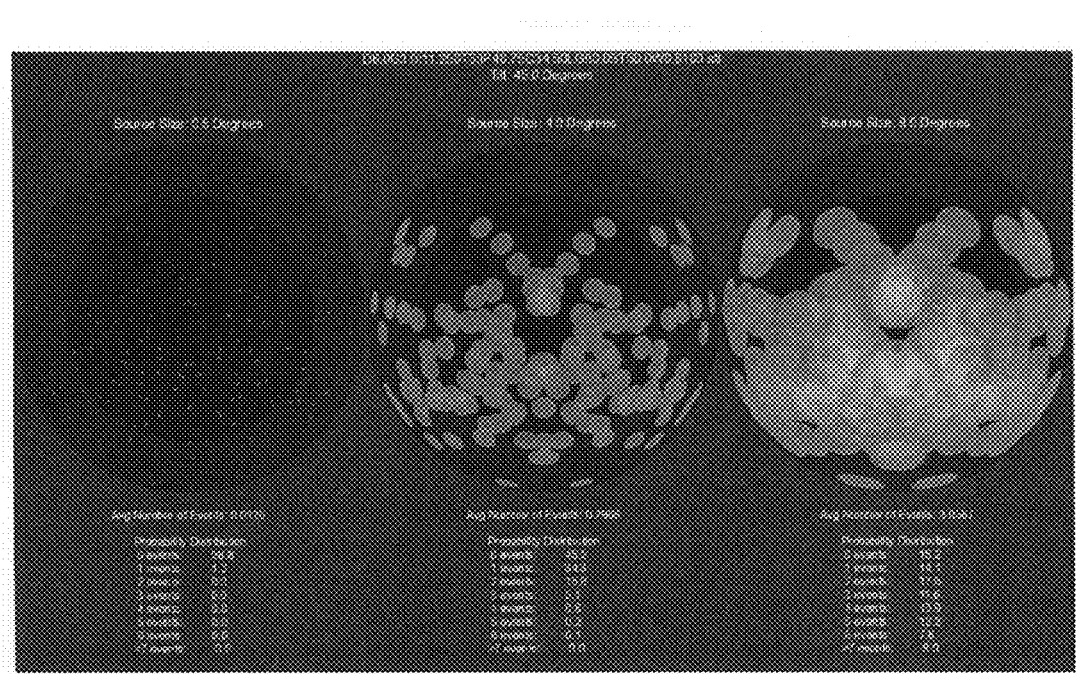

Maps like those in FIG. 15 may be generated to show the probability distribution of scintillation events. Animations of the maps of FIG. 15 may also be produced as the diamond is tilted through different orientations as the 4 quantities listed above can also be computed over an arbitrary number of tilts. FIGS. 16 and 17 show two examples of such tilt distributions with the diamond tilted at 22.5 and 45 degrees respectively. The black areas in FIG. 15 correspond to locations on the hemisphere (219) (shown in a 2-dimensional top-down representation so it is flattened) which produce 0 scintillation events for the specified source size. The lightest shade of color correspond to light source locations producing 1 scintillation event, the next lightest shade correspond to light source locations generating two scintillation events and so forth with fuller colors representing more events.

As can be seen in FIG. 15, the angular source size of the light source can be altered to provide for a more realistic determination of probability. In the first image of FIG. 15, pinpoint lights sources are used. As this means very little light would be incident on the diamond, only at limited very specific light source points is there any scintillation and the scintillation events are still relatively rare. This is logical since such a small source would generally have to strike a particular scintillation precisely to generate an event. However, as the light source is made larger (from about 4 degrees to about 8 degrees moving from left to right), the probability becomes greater over most of the stone.

As can be seen in FIG. 15, in this particular diamond, sourcing the light generally in the whiter area of the stone in the third view would likely produce a relatively large amount of scintillation. As this covers most of the diamond's table and provides for a wide range of coverage, this diamond would be expected to have a good scintillation potential compared to one which had less white and lighter colors present since the diamond will produce a relatively large number of scintillation events for a light source located in a relatively large area of the hemisphere (219).

In general, in the maps of FIGS. 15-17 diamonds with lots of white and lighter shades will be more scintillating than stones with mostly black and dark shades as there is an increased area where the light can be sourced to generate an increased number of scintillation events. In this type of map, the diamond's ability to produce scintillation events at a particular observation point but with the light and at a variety of sources are mapped at once allowing one to effectively compare scintillation generally without necessarily needing to have the image be animated to display the information.

While the above methods generally provide for the determination of scintillation events based on sub regions and at specific tilts, another embodiment of a method to compute the quantities listed above would be to place the source in every possible location on the hemisphere and ray trace the stone to specifically determine which facets are directing light to the user. If the hemisphere were divided into regions of 0.1 degree increments, this method would require that the stone be ray traced over 3.2 (900*3600) million times. Because this method would be computationally infeasible utilizing most currently available computational techniques, the following algorithm was developed which drastically speeds up the analysis.

First, the stone is ray traced to compute the list of direction vectors comprising it's angular spectrum. Data is then stored for each direction vector, including the area of the corresponding virtual facet, the dispersion of the virtual facet, the coordinates of the virtual facet, etc. A theoretical source (modeled as a disk) is placed at each of the regions of the hemisphere at a specified resolution (i.e., 0.1 degrees). For each location of the source, a test is performed to compute which direction vectors intersect it. Data is collected and stored for each of direction vector intersecting the source. After the tests are performed for each source location, the 4 quantities listed above are computed.

These theoretical sources are then used as disks on FIGS. 15-17 to provide for indications of probabilities that any random light source, when placed at the specified source on the hemisphere, would produce a certain number of scintillation events, therefore as opposed to the other FIGS., FIGS. 15-17 show the sources based on the hemisphere instead of the diamond itself. Alternatively to showing this information in graphical form, the average number of rays which intersect each source can be determined and then this can be provided as a numerical value of scintillation, effectively representing the likely number of scintillation events which would be seen when the diamond is exposed to any random light source.

Because the calculations are relatively simple and fast, this algorithm is able to compute the quantities above quickly and efficiently. The corresponding color-coded hemisphere maps are also generated at the same time.

While the systems and methods discussed herein have focused on their use in round brilliant cut diamonds, the systems and methods discussed herein can be used to characterize illumination effects in any shape and type of gemstone. These are often called "fancy" shapes and can include more common shapes, such as princess or oval cuts, but can also include proprietary cut shapes. Some shapes have less symmetry than the eightfold symmetry of the round diamond and others more, for example, fourfold and nine-fold symmetry. Therefore, the angular spectrum of some fancy cuts may not be as rich as it is for the round brilliant cut and additional angular ranges in elevation and in azimuth could be necessary to sufficiently assess the illumination properties. It is also possible to have fancy cuts with richer angular spectra than the angular spectrum of round brilliants also requiring relative consideration changes.

Because of the difference in shape, the maps and concepts developed in our research can still be applied for evaluating them, however, generally shapes need to be internally compared with similar shapes, as opposed to comparing across shapes. While comparisons across shapes can provide that certain cuts are generally more scintillating, that is often not as valuable in grading as determining which cuts within that shape provide for better scintillation.

While the invention has been disclosed in connection with certain preferred embodiments, this should not be taken as a limitation to all of the provided details. Modifications and variations of the described embodiments may be made without departing from the spirit and scope of the invention, and other embodiments should be understood to be encompassed in the present disclosure as would be understood by those of ordinary skill in the art.

The invention claimed is:

1. A method to evaluate scintillation in gemstones, the method comprising:
   acquiring the angular spectrum of a gemstone by tracing rays to the gemstone from a point of observation in relation to the gemstone;
   propagating the rays in the stone till they exit the stone;
   determining a region of a hemisphere arranged about said gemstone that said rays intersect; and
   coding an image of a virtual facet propagating said ray according to said region that said rays intersect.

2. The method of claim 1 wherein said gemstone is a diamond.

3. The method of claim 1 wherein said point of observation is located above a table of said gemstone.

4. The method of claim 1 wherein said region is located at a polar angle of between about 45 degrees and about 75 degrees.

5. The method of claim 4 wherein said region is one of a plurality of regions within said polar angle range.

6. The method of claim 5 wherein said regions in said plurality are arranged as concentric arcs.

7. The method of claim 5 wherein said regions in said plurality are arranged as truncated pie sections.

8. The method of claim 5 wherein said plurality of regions comprises 6 regions.

9. The method of claim 1 wherein said coding comprises color coding.

10. The method of claim 1 further comprising:
    tilting said gemstone relative said point of observation; and
    repeating said steps of propagating, determining and coding.

11. The method of claim 10 further comprising:
    presenting the results of said coding in a matrix of images where each of said images in said matrix corresponds to a different tilt of said gemstone.

12. The method of claim 10 further comprising:
    presenting said matrix of images in a sequence to provide an animation.

13. A system for evaluating scintillation in gemstones, the system comprising:
    a computer, said computer being provided with a virtual image of a gemstone;
    means in said computer for acquiring the angular spectrum of a gemstone by tracing rays to the gemstone from a point of observation in relation to the gemstone;
    means in said computer for determining a region of a virtual hemisphere arranged about said gemstone that said rays intersect; and
    means in said computer for coding an image of a virtual facet propagating each of said rays according to said region that said rays intersect.

14. A method for generating a graphical display of scintillation potential of a gemstone wherein the display comprises a color-coded image, the method comprising:
    providing an image of a gemstone, said image showing virtual facets of said gemstone;
    acquiring the angular spectrum of a gemstone by tracing rays to the gemstone from a point of observation in relation to the gemstone;
    determining a region of a virtual hemisphere arranged about said gemstone that each of said rays intersect; and
    color coding said image of a virtual facet propagating said ray according to said region that said ray intersects.

15. The display of claim 14 further comprising:
    a plurality of color-coded images, each of said images being generated by providing, acquiring, determining, and color-coding said gemstone with a different point of observation.

16. The display of claim 15 wherein said images are presented in a matrix.

17. The display of claim 15 wherein said images are presented sequentially in an animation.

18. A method for generating a graphical display of scintillation potential of a gemstone wherein the display comprises a color-coded image, the method comprising:
    acquiring the angular spectrum of a gemstone by tracing rays to the gemstone from a point of observation to said gemstone;
    determining a region of a virtual hemisphere arranged about said gemstone that each of said rays intersect;
    selecting a source on said virtual hemisphere;
    coding an image according to how many rays intersect that region;
    repeating said steps of selecting and coding for a plurality of sources.

19. A method for evaluating the scintillation of a gemstone, the method comprising:
    acquiring the angular spectrum of a gemstone by tracing rays to the gemstone from a point of observation to said gemstone;
    determining a region of a virtual hemisphere arranged about said gemstone that each of said rays intersect;
    selecting a source on said virtual hemisphere;
    determining how many rays intersect that source;
    repeating said steps of selecting and determining for a plurality of sources on said hemisphere; and
    evaluating the scintillation of said gemstone based on said repeating.

20. The method of claim 19 wherein said evaluation comprises determining the average number of intersections across all said sources.

21. The method of claim 19 wherein an image of said hemisphere is coded based on the number of rays that intersect each said source.

* * * * *